US012769090B2

(12) United States Patent
Lin et al.

(10) Patent No.: US 12,769,090 B2
(45) Date of Patent: Oct. 20, 2026

(54) OTOSCOPE

(71) Applicant: GUANGZHOU LUXVISIONS INNOVATION TECHNOLOGY LIMITED, Guangzhou City (CN)

(72) Inventors: Chih-Ju Lin, Guangzhou City (CN); Chen-Fu Huang, Guangzhou City (CN)

(73) Assignee: GUANGZHOU LUXVISIONS INNOVATION TECHNOLOGY LIMITED, Guangzhou City (CN)

( * ) Notice: Subject to any disclaimer, the term of this patent is extended or adjusted under 35 U.S.C. 154(b) by 85 days.

(21) Appl. No.: 18/918,083

(22) Filed: Oct. 17, 2024

(65) Prior Publication Data

US 2025/0248599 A1 Aug. 7, 2025

(30) Foreign Application Priority Data

Feb. 5, 2024 (CN) ......................... 202410165793.6

(51) Int. Cl.
*G02B 9/60* (2006.01)
*A61B 5/00* (2006.01)
*G02B 23/24* (2006.01)

(52) U.S. Cl.
CPC .............. *G02B 9/60* (2013.01); *A61B 5/0082* (2013.01); *G02B 23/2407* (2013.01)

(58) Field of Classification Search
CPC ........ A61B 1/227; A61B 1/2275; G02B 9/60; G02B 13/0045; G02B 23/2407
USPC ........................................ 359/764, 766, 767
See application file for complete search history.

(56) References Cited

U.S. PATENT DOCUMENTS 4,183,624 A * 1/1980 Rogers ................. G02B 25/001 359/767
7,354,399 B2 * 4/2008 Strom .................... A61B 1/227 600/200
2005/0027169 A1 * 2/2005 Goldfain ............ A61B 1/00188 600/200
(Continued)

FOREIGN PATENT DOCUMENTS

CN 209437209 9/2019
TW M536525 2/2017
(Continued)

OTHER PUBLICATIONS

Rustin G. Kashani et al., "Shortwave infrared otoscopy for diagnosis of middle ear effusions: a machine-learning-based approach", Scientific Reports, Jun. 2021, pp. 1-10.

*Primary Examiner* — Eduardo C Robert
*Assistant Examiner* — Anna V. Little
(74) *Attorney, Agent, or Firm* — JCIPRNET

(57) ABSTRACT

Provided is an otoscope that includes a sensing part. The sensing part includes a case, multiple light sources, and an optical sensing device. The optical sensing device is disposed in the case and sequentially includes a first lens element, a second lens element, a third lens element, a fourth lens element and a fifth lens element along an optical axis from an object side toward an image side. The first lens element, the third lens element and the fifth lens element have positive refracting power. The second lens element and the fourth lens element have refracting power. The otoscope has a total of five lens elements having refracting power, and the multiple light sources are configured to emit infrared light toward the object side.

19 Claims, 4 Drawing Sheets

(56) References Cited

U.S. PATENT DOCUMENTS

| | | | | |
|---|---|---|---|---|
| 2013/0267783 | A1* | 10/2013 | Davis | A61B 1/227 600/199 |
| 2015/0223678 | A1* | 8/2015 | Goldfain | A61B 3/1208 351/205 |
| 2016/0077310 | A1* | 3/2016 | Sudoh | G02B 15/142 359/764 |
| 2017/0027448 | A1* | 2/2017 | Carr | A61B 5/12 |
| 2018/0168440 | A1* | 6/2018 | Das | A61B 1/0669 |
| 2020/0107813 | A1* | 4/2020 | Moehring | A61B 1/2275 |
| 2021/0236089 | A1 | 8/2021 | Moehring et al. | |
| 2023/0161147 | A1* | 5/2023 | Kirma | A61B 1/00181 600/109 |
| 2023/0240523 | A1* | 8/2023 | Small | A61B 1/053 600/200 |

FOREIGN PATENT DOCUMENTS

| | | | | |
|---|---|---|---|---|
| TW | 202319016 | | 5/2023 | |
| WO | WO-2023147346 | A1 * | 8/2023 | A61B 1/227 |

* cited by examiner

OTOSCOPE

CROSS-REFERENCE TO RELATED APPLICATION

This application claims the priority benefit of China application serial no. 202410165793.6, filed on Feb. 5, 2024. The entirety of the above-mentioned patent application is hereby incorporated by reference herein and made a part of this specification.

BACKGROUND

Technical Field

The disclosure relates to an optical detection device, in particular to an otoscope.

Description of Related Art

When a foreign object enters a human ear, conditions such as ear canal infection, otitis media, and hearing loss may be caused. In clinical practice, the fastest and most direct way to examine is to place an otoscope into the external auditory canal for observation. In principle, conditions outside the eardrum may be observed. In recent years, otoscopes have also developed into digital otoscopes. Real-time recording may be performed during observation. Doctors may also keep a more appropriate distance from the subject.

However, the illumination light source and the wavelength band to capture image that are used by a current otoscope are mainly visible light. With the characteristics of visible light, information from the middle ear on the other side of the eardrum is impossible to be clearly observed. In addition, Graphical otoscope images require an image sensor, and therefore the cost is higher.

SUMMARY

The disclosure provides an otoscope. Optical detection of the infrared light band may be provided, and the cost is low.

According to an embodiment of the disclosure, an otoscope is provided that includes a sensing part. The sensing part includes a case, multiple light sources, and an optical sensing device. The optical sensing device is disposed in the case and sequentially includes a first lens element, a second lens element, a third lens element, a fourth lens element and a fifth lens element along an optical axis from an object side toward an image side. The first lens element, the third lens element and the fifth lens element have positive refracting power. The second lens element and the fourth lens element have refracting power. The otoscope has a total of five lens elements with refracting power, and the multiple light sources are configured to emit infrared light toward the object side.

Based on the above, the otoscope provided by the embodiment of the disclosure includes the optical sensing device. The optical sensing device includes 5 lens elements with refracting power. Based on this, a light reflected and scattered from a target to be measured may be focused on an optical sensor, and the measurement accuracy can be improved. In addition, the optical sensor may be implemented with a photodiode. An image sensor of a traditional otoscope may be replaced, and the cost is reduced significantly.

In order to make the features and advantages of the disclosure more comprehensible, the following examples are given and described in detail with the accompanying drawings as follows.

DESCRIPTION OF THE EMBODIMENTS

Figure 1:
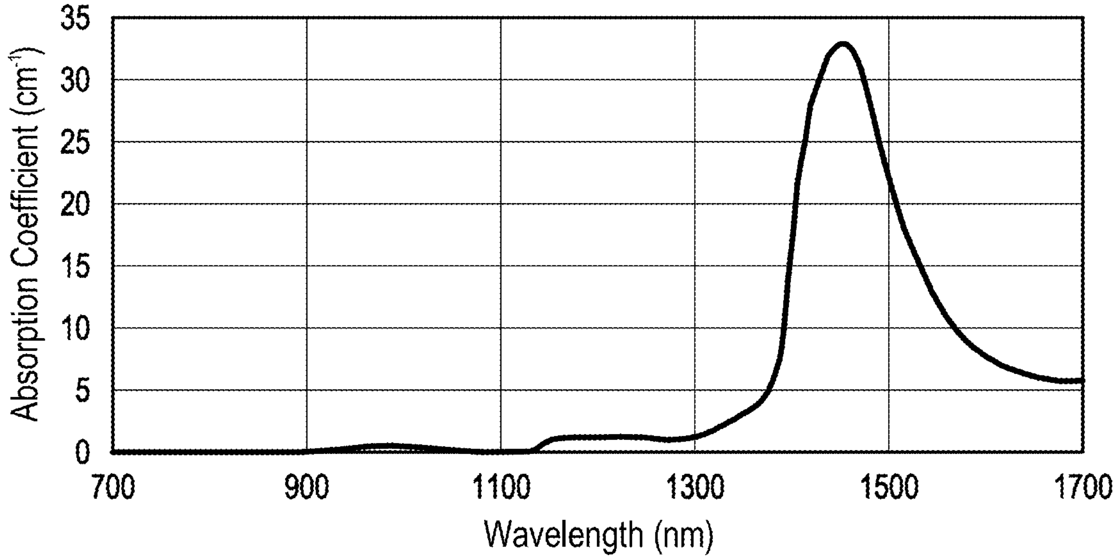
FIG. 1 is a graph of an absorption coefficient of water in a near infrared band and a short infrared band.

Referring to FIG. 1, a graph of an absorption coefficient of water in a near infrared band and a short infrared band is shown. At around 1450 nm in an infrared light range, an absorption coefficient of water molecules has a partial maximum value. Clinically, the fluid accumulated in otitis media is a tissue fluid, the main component of the tissue fluid is water. In other words, if there is effusion in otitis media, the utilization of infrared light to perform illumination may improve the accuracy of clinical determination.

Figure 2:
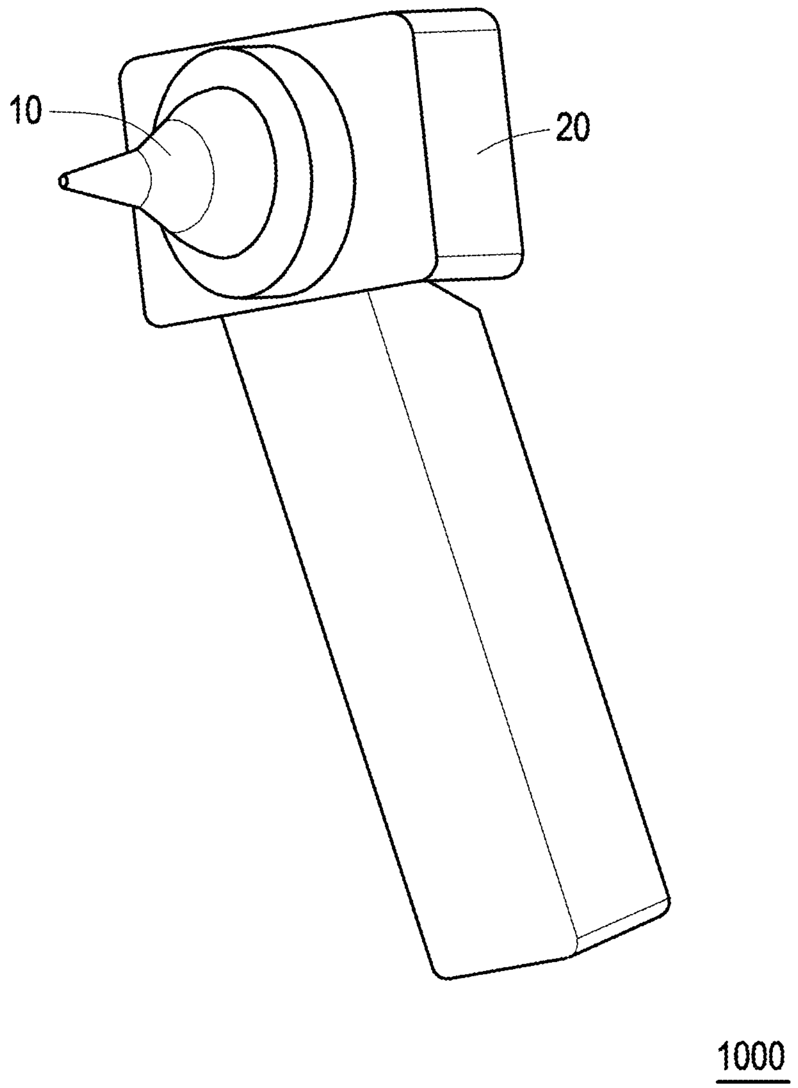
FIG. 2 is a schematic diagram of an otoscope according to an embodiment of the disclosure.
Figure 3:
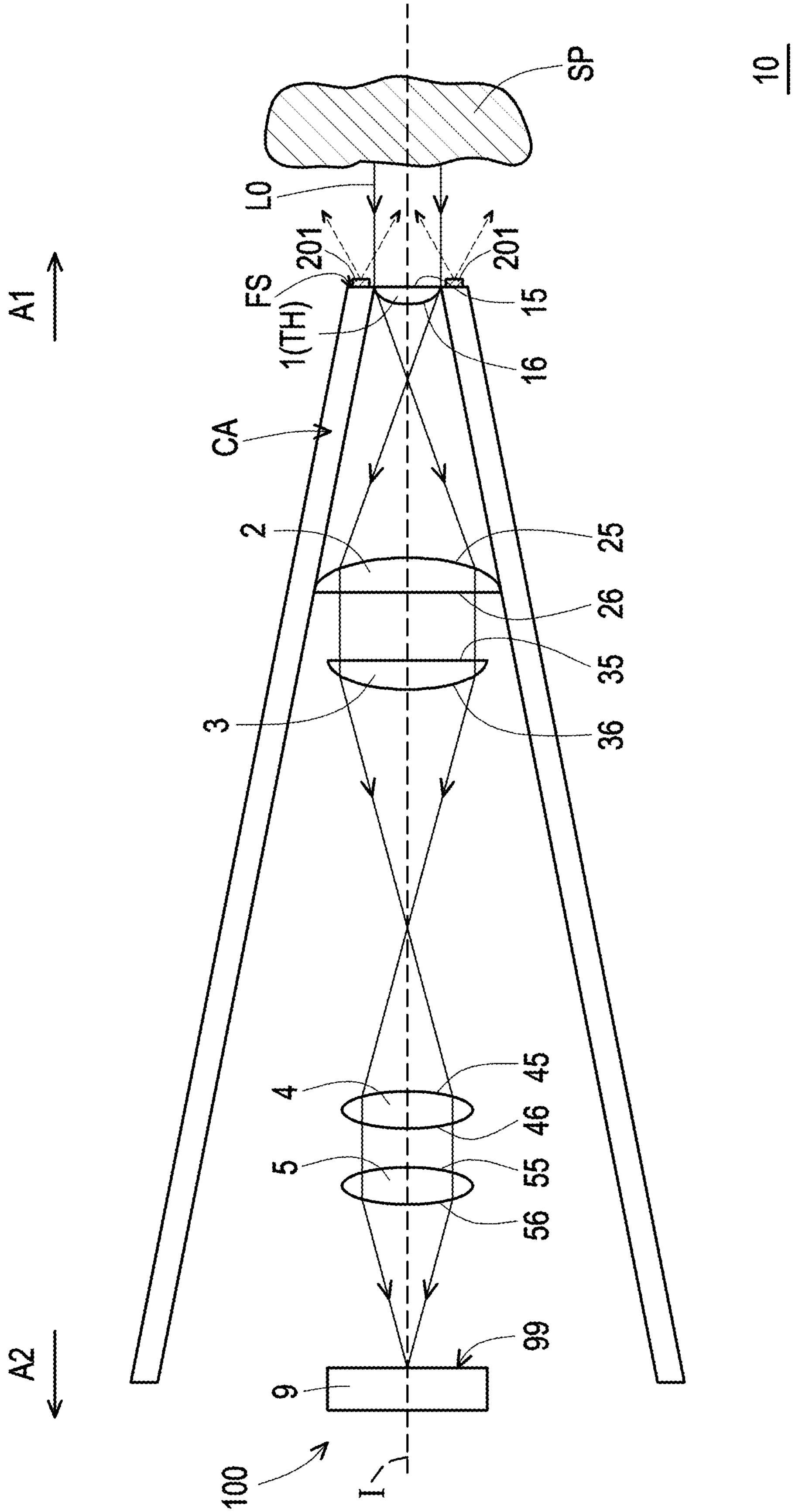
FIG. 3 is a schematic diagram of a sensing part according to an embodiment of the disclosure.
Figure 4:
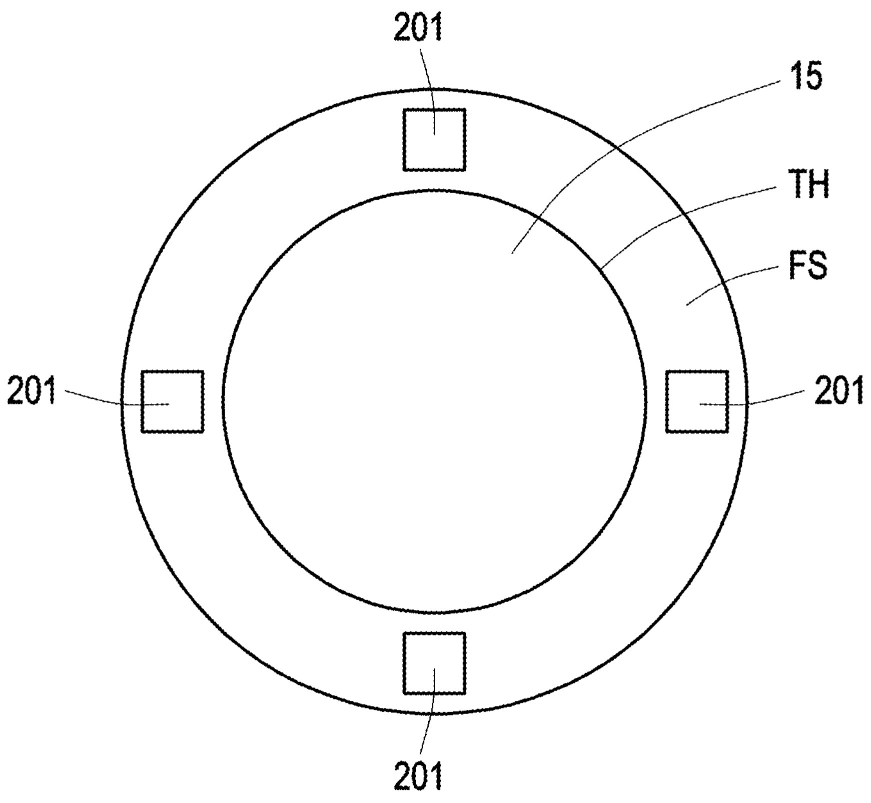
FIG. 4 is a schematic diagram of a front end of a sensing part according to an embodiment of the disclosure.

Referring to FIG. 2, FIG. 3 and FIG. 4, FIG. 2 is a schematic diagram of an otoscope according to an embodiment of the disclosure, FIG. 3 is a schematic diagram of a sensing part according to an embodiment of the disclosure, and FIG. 4 is a schematic diagram of a front end of a sensing part according to an embodiment of the disclosure.

The otoscope 1000 includes a sensing part 10 and a control part 20. The sensing part 10 includes a case CA, multiple light sources 201, and an optical sensing device 100. The case CA includes a light entrance hole TH and a front-end plane FS that surrounds the light entrance hole TH.

The light sources 201 that are disposed on the front-end plane FS are configured to emit infrared light to illuminate a target to be measured SP. The number of light sources 201 may be greater than or equal to 2, and a distance between each of the light sources 201 is the same to provide sufficient and uniform illumination light. A light to be measured LO that is reflected and scattered from the target to be measured SP enters the optical sensing device 100. The target to be measured SP may be, for example, a tissue in the ear, a foreign object in the ear, water in the ear, etc.

Since the length of a human external auditory canal is about 25 mm, and the inner diameter is 4 to 8 mm, the maximum diameter (outer diameter) of the front-end plane FS may be greater than or equal to 3 mm to allow the otoscope 1000 to be placed a certain distance into the external auditory canal. Interference from external light may be avoided, and the condition in the auditory canal may also be more clearly observed.

In the embodiment, the light sources 201 may be infrared light LEDs, and may have a partial maximum luminous intensity within a wavelength range of 900 nm to 1700 nm. Based on this, for substances with low absorption coefficients in the visible light band, or substances that are transparent in the visible light band (such as water), whether there is a foreign object or water in the ear may be determined through a method of illuminating infrared light.

In some exemplary embodiments, the light sources 201 may have a partial maximum luminous intensity within a wavelength range of 1400 nm to 1500 nm. For example, an LED with a maximum luminous intensity at 1450 nm may have a full width at half maximum of about 100 nm. Based on this, the characteristics of water molecules having a higher absorption coefficient around 1450 nm may be utilized to improve sensing accuracy.

The optical sensing device 100 is disposed in the case CA and sequentially includes a first lens element 1, a second lens element 2, a third lens element 3, a fourth lens element 4, a fifth lens element 5, and an optical sensor 9 along an optical axis I of the optical sensing device 100 from an object side A1 toward an image side A2.

The optical sensor 9 may be, for example, a photodiode. An optical signal may be converted into an electrical signal, and the cost is significantly reduced compared to an image sensor in a traditional otoscope. The material of the optical sensor 9 may include indium gallium arsenide (InGaAs), plumbous sulfide (PbS), and silicon carbide (SiC). For example, it may also be some novel photodiode materials, such as organic photodiodes, polyethyleneimine (PEI), quantum dot photodiodes, silver telluride ($Ag_2Te$), bismuth selenide ($Bi_2Se_3$), perovskite photodiodes, methylammonium lead halide (MAPbX3) and the like. InGaAs with stable characteristics and low noise is selected for the optical sensor 9 of the embodiment of the disclosure compared to silicon that can only detect light wavelengths within a range of 190 nm to 1100 nm. The sensing wavelength thereof is from 900 nm to 1700 nm. The light illuminous wavelengths of the light sources 201 are covered.

The light to be measured LO that is generated by the light sources 201 and reflected and scattered by the target to be measured SP enters the optical sensing device 100 and sequentially goes through the first lens element 1, the second lens element 2, the third lens element 3, the fourth lens element 4 and the fifth lens element 5 before being focused on a light receiving surface 99 of the optical sensor 9. The first lens element 1, the second lens element 2, the third lens element 3, the fourth lens element 4 and the fifth lens element 5 individually has an object-side surface 15, 25, 35, 45, and 55 facing the object side A1 and allowing imaging light to pass through, and an image-side surface 16, 26, 36, 46, and 56 facing the image side A2 and allowing imaging light to pass through.

The first lens element 1 is spherical and has a positive refracting power. The object-side surface 15 thereof is a flat surface, the image-side surface 16 is a convex surface, and the first lens element 1 is disposed at the light entrance hole TH of the case CA. The second lens element 2 is spherical and has a positive refracting power. The object-side surface 25 thereof is a convex surface, and the image-side surface 26 is a flat surface. The third lens element 3 is spherical and has a positive refracting power. The object-side surface 35 thereof is a flat surface, and the image-side surface 36 is a convex surface. The fourth lens element 4 is spherical and has a positive refracting power. The object-side surface 45 thereof is a convex surface, and the image-side surface 46 is a convex surface. The fifth lens element 5 is spherical and has a positive refracting power. The object-side surface 55 is a convex surface, and the image-side surface 56 is a convex surface.

Other detailed optical data of the optical sensing device 100 are shown in Table 1. The focus range thereof is less than or equal to 25 mm.

TABLE 1

| Element | Surface | Radius of Curvature (mm) | Spacing (mm) | Refractive Index | Refracting power ($m^{-1}$) |
|---|---|---|---|---|---|
| Object | | Infinite | 5.00 | | |
| First Lens Element 1 | Object-Side Surface 15 | Infinite | 0.80 | 1.814 | 250.0 |
| | Image-Side Surface 16 | −3.40 | 14.30 | | |
| Second Lens Element 2 | Object-Side Surface 25 | 6.20 | 2.60 | 1.501 | 83.3 |
| | Image-Side Surface 26 | Infinite | 4.00 | | |
| Third Lens Element 3 | Object-Side Surface 35 | Infinite | 1.45 | 1.501 | 50.0 |
| | Image-Side Surface 36 | −10.34 | 28.35 | | |
| Fourth Lens Element 4 | Object-Side Surface 45 | 9.80 | 2.00 | 1.501 | 100.0 |
| | Image-Side Surface 46 | −9.80 | 4.00 | | |
| Fifth Lens Element 5 | Object-Side Surface 55 | 9.80 | 2.00 | 1.501 | 100.0 |
| | Image-Side Surface 56 | −9.80 | 9.31 | | |
| Optical Sensor 9 | Optical Receiving Surface 99 | Infinite | | | |

In Table 1, the spacing of the object-side surface 15 (0.80 mm as shown in Table 1) is the thickness of the first lens element 1 on the optical axis I, and the spacing of the image-side surface 16 (14.30 mm as shown in Table 1) is the distance between the image-side surface 16 of the first lens element 1 and the object-side surface 25 of the second lens element 2 on the optical axis I, that is, the gap between the first lens element 1 and the second lens element 2 on the optical axis I, and so on.

The first lens element 1 that is disposed at the light entrance hole TH of the case CA may not only refract light but also avoid the optical sensing device 100 from being internally contaminated. The optical effective diameter of the second lens element 2 is larger than the optical effective diameter of the first lens element 1. Based on this, the light to be measured LO that transmits the first lens element 1 may be incident on and transmits the second lens element 2 completely. Such a configuration can avoid light loss. Since the refracting power of the first lens element 1 is greater than the refracting power of the second lens element 2, the light to be measured LO that transmits the first lens element 1 and the second lens element 2 is firstly shrunk and then expanded. In addition, the surfaces of the first lens element 1 to the surfaces of the fifth lens element 5 are coated with an anti-reflection layer for a wavelength range of 900 nm to 1700 nm.

In summary, the otoscope provided by the embodiment of the disclosure includes the optical sensing device. The optical sensing device includes 5 lens elements having refracting power. Based on this, the light to be measured that is reflected and scattered from the target to be measured may be focused on the optical sensor. The measurement accuracy may be improved, and the optical sensor may be implemented by a photodiode. An image sensor of a traditional otoscope is replaced. The cost is significantly reduced.

What is claimed is:

1. An otoscope, comprising a sensing part, wherein the sensing part comprises:

a case;

a plurality of light sources; and an optical sensing device, disposed in the case, and along an optical axis from an object side to an image side sequentially comprising:

a first lens element, having a positive refracting power;

a second lens element, having a refracting power;

a third lens element, having a positive refracting power;

a fourth lens element, having a refracting power; and a fifth lens element, having a positive refracting power, wherein the otoscope has a total of five lens elements having refracting power, and the plurality of light sources are configured to emit infrared light toward the object side, wherein the plurality of light sources have a partial maximum luminous intensity within a wavelength range of 900 nm to 1700 nm.

2. The otoscope according to claim 1, wherein the first lens element is plano-convex.

3. The otoscope according to claim 1, wherein the second lens element is plano-convex.

4. The otoscope according to claim 1, wherein the third lens element is plano-convex.

5. The otoscope according to claim 1, wherein the fourth lens element is biconvex.

6. The otoscope according to claim 1, wherein the fifth lens element is biconvex.

7. The otoscope according to claim 1, wherein the second lens element has a positive refracting power.

8. The otoscope according to claim 7, wherein the refracting power of the first lens element is greater than the refracting power of the second lens element.

9. The otoscope according to claim 1, wherein an optical effective diameter of the second lens element is larger than an optical effective diameter of the first lens element.

10. The otoscope according to claim 1, wherein the fourth lens element has the positive refracting power.

11. The otoscope according to claim 1, wherein the first lens element is spherical.

12. The otoscope according to claim 1, wherein the second lens element is spherical.

13. The otoscope according to claim 1, wherein the third lens element is spherical.

14. The otoscope according to claim 1, wherein the fourth lens element is spherical.

15. The otoscope according to claim 1, wherein the fifth lens element is spherical.

16. The otoscope according to claim 1, wherein the case comprises a light entrance hole and a front-end plane that surrounds the light entrance hole, the plurality of light sources are disposed on the front-end plane, and the first lens element is disposed at the light entrance hole.

17. The otoscope according to claim 1, wherein the plurality of light sources have the partial maximum luminous intensity within a wavelength range of 1400 nm to 1500 nm.

18. The otoscope according to claim 1, further comprising an optical sensor, wherein the optical sensor comprises indium gallium arsenide.

19. The otoscope according to claim 1, wherein a focus range of the otoscope is less than or equal to 25 mm.

* * * * *